United States Patent
Pagedas

[19]

[11] Patent Number: 5,741,301
[45] Date of Patent: Apr. 21, 1998

[54] SELF LOCKING SUTURE LOCK

[76] Inventor: Anthony C. Pagedas, 8401 W. Edgerton, Greenfield, Wis. 53129

[21] Appl. No.: 840,287

[22] Filed: Apr. 14, 1997

Related U.S. Application Data

[63] Continuation of Ser. No. 607,421, Feb. 28, 1996.

[51] Int. Cl.$^6$ ..................................................... A61B 17/04
[52] U.S. Cl. ............................. 606/232; 606/228; 606/148
[58] Field of Search .................................. 606/232, 233, 606/228, 193, 144, 145, 148, 142, 151, 155, 157, 158

[56] References Cited

U.S. PATENT DOCUMENTS

| | | | |
|---|---|---|---|
| 2,075,508 | 3/1937 | Davidson | 606/232 |
| 3,976,079 | 8/1976 | Samuels et al. | 606/232 |
| 5,370,661 | 12/1994 | Branch | 606/232 |
| 5,630,824 | 5/1997 | Hart | 606/232 |

*Primary Examiner*—Michael Buiz
*Assistant Examiner*—Daphna Shai
*Attorney, Agent, or Firm*—Wheeler Kromholz & Manion

[57] ABSTRACT

A self locking suture lock having first and second stitch lock openings designed to receive suture thread in only one direction, thereby locking the thread against withdrawal after the stitch to complete and lock it without the need for a surgical knot. A tongue in the first and second openings will allow passage through each opening from one side to the other side but will not allow passage in the opposite direction. The suture needle insertion side of each opening may be distinctively colored so that a surgeon will know which side of the suture lock will accept the suture thread. A notch may also be formed in each opening to further prevent the removal of the surgical thread. The suture lock is fabricated from an absorbable material that will dissolve at the surgical site over a period of time.

2 Claims, 2 Drawing Sheets

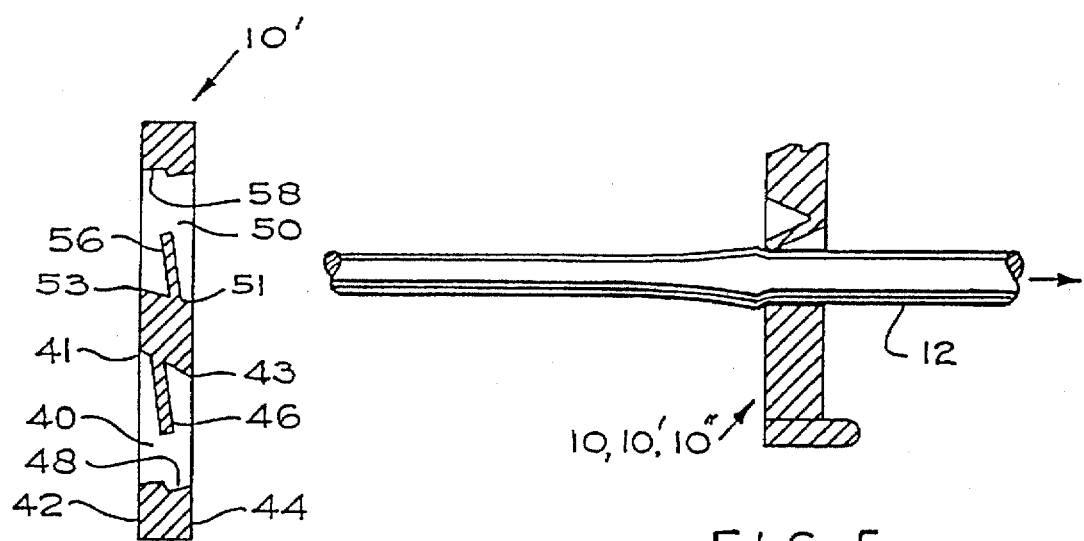
FIG. 4
FIG. 5
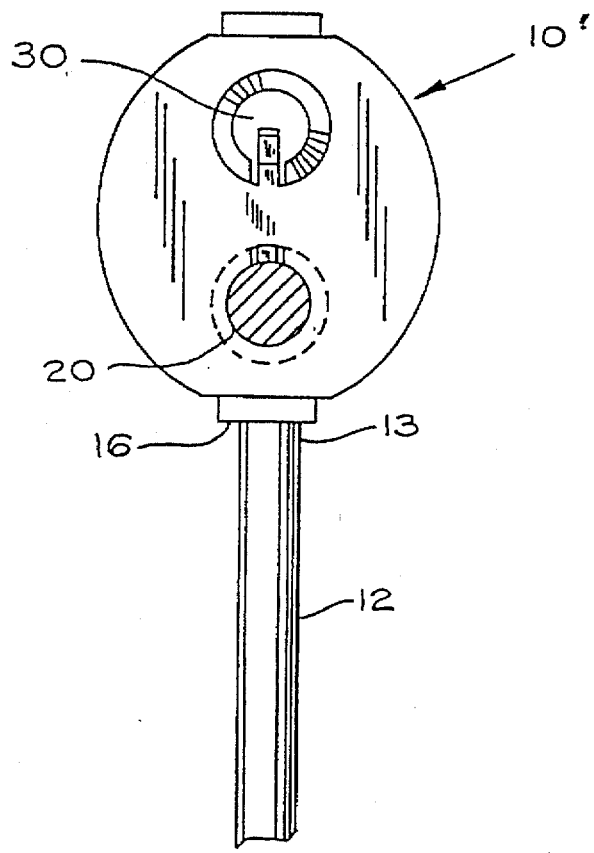
FIG. 6

SELF LOCKING SUTURE LOCK

This application is a continuation of application Ser. No. 08/607,421 filed 28 Feb. 1996 which application is now pending.

BACKGROUND OF THE INVENTION

The need for this invention arises from surgical practice and procedures, particularly surgical practice and procedures using laparoscopic instruments. Utilizing laparoscopic instruments involves making two or more small incisions in the area of the surgical site. A laparoscopic video camera is inserted into one of the incisions to view the field of the operation inside the patient and laparoscopic surgical instruments are inserted in other incisions and manipulated from outside the patient's body using a video screen visualization, usually enlarged, to guide the work.

Anything that can reduce the number of steps to be performed during surgery can markedly reduce the stress, both on the patient and on the doctor. Surgeons performing such operations are under considerable stress because remote manipulation of the surgical instruments using a video screen for visualization, rather than seeing the site of the operation directly, requires the learning of a great many techniques that are radically different from those performed when the surgical site is open to view. The required techniques include indirect hand-eye coordination and the cooperation between surgeons to place and secure sutures at the surgical site.

The placing of sutures during a laparoscopic surgical procedure typically requires two surgeons. The surgeons must cooperate in a multi-step process performed with multiple surgical instruments to manipulate the suture needle and the suture. The needle and suture are passed back and forth from one to the other, while placing the sutures and while tieing one or more knots. This improvement, as well as my invention disclosed in U.S. Pat. No. 5,413,585, arose from the difficulty of such manipulations.

SUMMARY OF THE INVENTION

Similar to my invention as disclosed in U.S. Pat. No. 5,413,585, the present invention relies primarily on a one-piece specialized lock having a body with two openings. In contrast to the embodiments taught in U.S. Pat. No. 5,413,585, both openings in the present embodiment are stitch lock openings. Passage of the suture material through each stitch lock opening is facilitated by making the opening in a highly visible color and by forming the opening with a cone-shaped approach to help guide the suture needle through the opening. The exit opening in contrast, is little larger than the diameter of the suture itself so that it is neither very visible nor very approachable by the suture needle, to guard against suture needle insertion in the wrong direction.

Within the stitch lock openings, flexible tongues project into each opening and are inclined in the direction that the suture needle follows when it is inserted first into the large cone-shaped approach opening to later pass through the smaller exit opening. Each flexible tongue freely allows the suture material to pass, deflecting the tongue in the process, but the springiness of each tongue and the engagement of each tongue edge with the suture prevent withdrawal of the suture material. The suture is under tension so the pull deflects the tongue upward in the opening, jamming the suture material against the side of the opening. The equivalent of a knot is achieved.

The principal advantage of my improvement is that my improved self locking suture lock can be passed independently through a laparoscopic tube inserted into the body cavity of the patient near the surgical site. After my improved self locking suture lock is inserted into the body cavity, the suture material can be passed through and locked into the first suture lock opening. Thus, it is not required that the suture material be passed through or attached to the self locking suture lock before insertion into the laparoscopic tube. Thus the surgeon is free to insert either my improved self locking suture lock or the suture material into the body cavity in any order that is desired. Furthermore, additional improved self locking suture locks may be passed through the laparoscopic tube into the body cavity and placed on the suture as the suturing progresses thus reducing the number of sutures that must be introduced to the operative site. Before each additional suture, the suture needle is passed through the first suture lock opening in the additional self-locking suture lock. This step is performed within the body cavity by manipulations which are conducted through the laparoscopic tubes.

A needle is conventionally attached at the forward end of the suture material. The needle is passed through the first stitch lock opening and the suture material is then pulled through the first opening until the desired amount of suture material lies between the suture needle and my improved self-locking suture lock. After the suture material is properly positioned through the first stitch lock opening with respect to the suture needle, the suture needle is brought through the tissue to be sutured in the conventional way after which the suture needle is passed through the second suture lock opening in my improved self locking suture lock.

In another embodiment, the suture material is connected to the self locking suture lock, preferably at its base. Thus the self-locking suture lock and suture material can be passed through the laparoscopic tube into the surgical site as a unit. While the end of the suture material is preferably connected to the base of the self-locking suture lock in this embodiment, it is to be understood that any portion of the surgical thread could be connected or attached to any portion of the self-locking suture lock.

To begin suturing, the suture material is passed through the tissue to be sutured. When the surgeon wants to close a line of tissue or finish a cuff, the suture material is passed through the lower suture lock opening of the self-locking suture lock. When the suturing is complete, the surgeon passes the suture material through the upper suture lock opening of the self-locking suture lock in order to complete the process. If additional sutures are required and a sufficient amount of suture material remains, the surgeon can pass a second self-locking suture lock not having the suture material attached thereto through the laparoscopic tube into the surgical site. The suture material would then be passed through the first suture lock opening as described above. Alternatively, and if a sufficient amount of suture material is not available, the surgeon can pass a second self-locking suture lock having the suture material connected thereto into the surgical site.

Desirably the flexible suture material that trails from the attached needle may be braided in a know way to have a very slight roughness to the surface in the direction from the end of the suture toward the needle, but to be smooth in the direction from the needle to the end of the suture. Such suture material is known and is particularly appropriate for use with my self locking suture lock because the flexible tongue can grip the suture even more firmly if it is of this character. The deflection of the tongue when the suture is passed through the stitch lock opening pulls the tongue against the opening when the suture material is stressed in the other direction thereby locking suture material firmly into place without any surgical knot. Such a knot may be added at the surgeon's discretion; however, a knot is not required to practice my invention.

An additional advantage of my improved suture lock is that after the first stitch has been locked into place as described, the needle end of the suture remains free. A second suture lock may be placed on the suture at a suitable distance from the first suture lock and the suture procedure can be repeated by passing the suture needle through additional tissue and again inserting the needle into the approach passage of the second suture lock opening, passing it through, and pulling it tight. This second stitch is now locked into place while only a single piece of suture material has been used, eliminating the additional steps of removing the first suture needle and the remaining suture material from the surgical site, introducing a second suture and suture needle, etc. The number of sutures depends on suture material length and the location of the needle stitches.

By utilizing my invention, many steps traditionally involved with suturing during laparoscopic surgery have been eliminated. These include at least the steps of two surgeons cooperating to loop the suture about a clamping instrument and then the two surgeons cooperating to pull the ends of the suture to tighten a knot, and in many cases the steps of introducing new sutures are also reduced.

Thus my improved self locking suture lock eliminates a number of complex knot tieing steps and in the right circumstances can reduce the number of sutures required to be introduced to a surgical site, further reducing the number of steps to be performed by the surgeon and reducing the complexity of those steps so that the manipulations become easier. It is always an advantage to make the surgical manipulations easier, both to reduce stress on the surgeon and to reduce the possibility that the instruments or needle will penetrate where it is not wanted. Simpler manipulation assists in this goal.

In its preferred embodiment, my improved self locking suture lock is manufactured or fabricated from an absorbable material such as polyglycolic acid (a homopolymer of glycolic acid) or a copolymer of glycolide and L-lactide. Sutures used with all surgeries are also manufactured from these materials and are sold under the trademarks DEXON®, VICRYL®, and TI-CRON®. These materials dissolve over a predetermined period of time at the surgical site. My improved self locking suture lock will dissolve as well thus eliminating the requirement of the sutures and suture lock being removed after the predetermined period of time.

These and other benefits of the present invention will become apparent from the following detailed description taken in conjunction with the accompanying drawings.

DESCRIPTION OF THE DRAWINGS

FIG. 4 is a cross-sectional view of an alternative embodiment of my invention.

FIG. 5 is a partial cross-sectional view of my improved invention and suture material having a gathered portion.

FIG. 6 is a front elevational view of a second alternative embodiment of my improved self locking suture lock.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
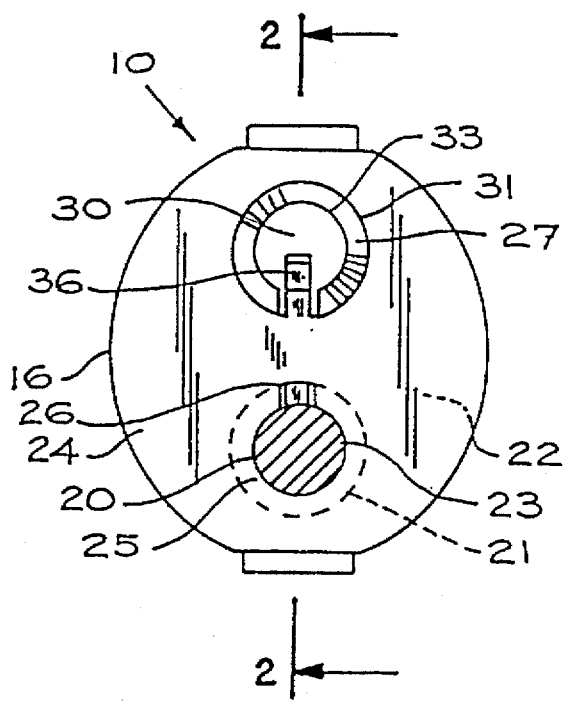
FIG. 1 is a front elevational view of my improved self locking suture lock.

Referring to FIG. 1, my improved self locking suture lock 10 includes a body 16 having a first stitch lock opening 20, a second stitch lock opening 30, a front side 22, and back side 24. The first opening 20 is cone-shaped, with the diameter of the first opening 20 at edge 21 on the front side 22 being larger than the diameter of the first opening 20 at edge 23 on the back side 24. The diameter of the first opening 20 on the back side 24 is slightly smaller than the diameter of suture thread 12. The second opening 30 is also cone-shaped, with the diameter of the second opening 30 at edge 31 on the back side 24 being larger than the diameter of the second opening 30 at edge 33 on the front side 22. The diameter of the second opening 30 on the back side 24 is slightly larger than the diameter of suture thread 12.

Referring again to FIG. 1, the area 25 on the front side 20, of the body 16 around the first opening 20 between edges 21 and 23 and the area 27 on the back side 24 around the second opening 30 between edges 81 and 33 may be colored differently than the rest of the body 16 in order to distinctly mark the difference from the front side 22 and the back side 24. This is so that the surgeon may distinguish the front side 22 from the back side 24 of the suture lock body 16. This helps to prevent the surgeon from inserting the suture thread 12 into either opening 20 or 30 in the wrong direction.

Figure 2:
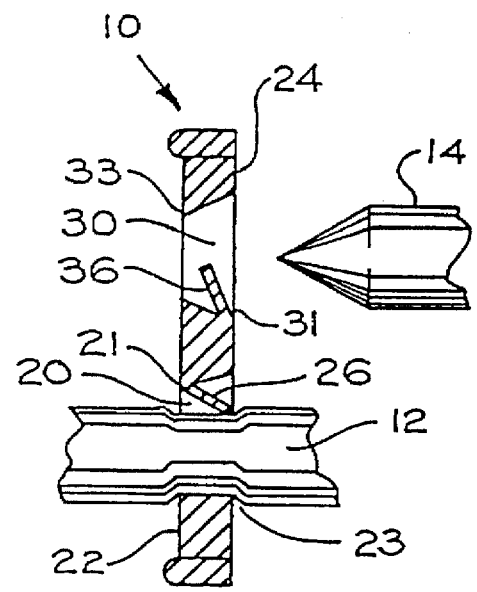
FIG. 2 is a cross-sectional view of my improved invention taken on line 2—2 of FIG. 1.

Tongues, 26 and 36, are located within openings 20 and 30 respectively. Each tongue 26 and 36 is a resilient piece of body material that is connected integrally to the body 16 at outer edges 21 and 31 of openings 20 and 30 respectively. Referring to FIG. 2 and with respect to the first suture lock opening 20, the base of tongue 26 is located nearer to the front side 22 than the back side 34. The tongue 26 extends inwardly from outer edge 21 at an angle toward a back side 24. With respect to second suture lock opening 30, tongue 36 is located nearer to the back side 24 than to the front side 22. The tongue 36 extends inwardly from the outer edge 31 at an angle toward the front side 22. The cone-shapes of the first and second openings 20 and 30 create approaches that allow for easy passage of the suture needle 14 and suture material 12 through the openings 20 and 30. As the needle 14 and suture thread 12 are passed through each respective opening, the respective tongues 26 and 36 deflect further toward side opposite where each tongue is attached. The deflection of tongue 26 allows passage of suture needle 14 and suture thread 12 through the first opening 20 from the front side 22 to the back side 24, but prevents passage of suture thread 12 back through the first opening 20 from back side 24 to front side 22. The deflection of tongue 36 allows passage of the suture needle 14 and suture thread 12 through the second opening 30 from back side 24 to the front side 22, but prevents passage of the suture thread 12 back through the second opening 30 from front side 22 to back side 24. The suture thread 12 is locked into my improved self locking suture lock 10 in this manner.

In its preferred embodiment, my improved self locking suture lock 10 is manufactured from an absorbable material such as polyglycolic acid (a homopolymer of glycolic acid) or a copolymer of glycolide and L-lactide. Sutures commonly used with all types of surgeries are also manufactured from these materials and are sold under the trademarks DEXON®, VICRYL®, and TI-CRON®. These materials dissolve over a predetermined period of time at the surgical site. My improved self locking suture lock 10 will dissolve at the surgical site as well thus eliminating the requirement of the suture material 12 and suture lock 10 being removed after the predetermined period of time.

Figure 3:
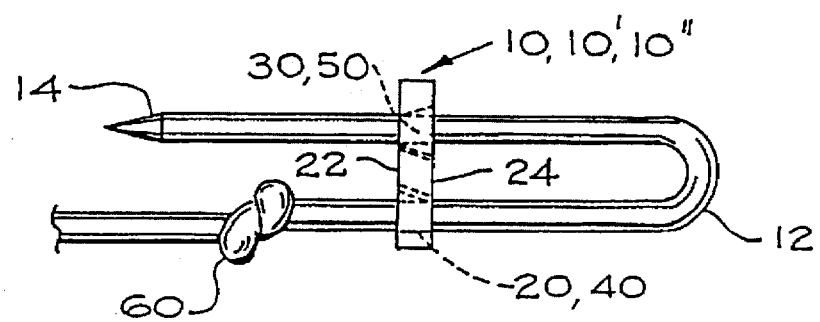
FIG. 3 is a side elevational view of my improved self locking suture lock, suture material, and a suture needle.

My improved self locking suture lock 10 works as follows. First, the self locking suture lock 10 is independently passed through a laparoscopic tube to the surgical site within the patient's body cavity. A conventional straight or curved suture needle 14 is connected permanently to the free end of the suture thread 12. The suture thread 12 can be either braided suture material or monofilament suture material. The strand of suture thread 12 with needle 14 can be passed through the laparoscopic tube either prior to the passing of the improved self locking suture lock or after the passing of the improved self locking suture lock. Next, the suture needle 14 is passed through the first opening 20 in the improved self locking suture lock 10. Alternatively, and if the surgeon should desire, the suture needle 14 and suture thread 12 could be passed through the first opening 20 prior to the insertion of either structure into the laparoscopic tube. Additionally, and as shown in FIG. 3, a knot 60 may be tied in the free end of the suture thread. While the knot 60 is not required to practice my invention, some surgeons have a higher degree of comfort with my device when a knot is used as shown.

Next, the suture needle 14 and suture thread 12 are brought through the tissue to be sutured in the conventional manner. Third, the suture needle 14 and suture thread 12 are threaded through the second stitch lock opening 30 of the improved self locking suture lock 10 from the back side 24 to the front side 22 and pulled as tight as needed. The suture is then complete, without the need for a surgical knot, and also without the need for a second surgeon.

Additionally, since the suture thread 12 remains free at the end where the suture needle 14 is attached, another self locking suture lock 10 may be introduced to the operative site, through the laparoscopic tube, and locked at a desired position on the same suture thread 12. Following that, another stitch may be made and locked in the same manner as described above. The number of stitches is limited only by the length of suture thread 12 and the length of suture thread 12 in each stitch.

Referring to FIG. 4, an alternative body of my improved self locking suture lock 10' is shown. The first opening 40 has a tongue 46, an outer edge 41, and an inner edge 43, and a notch 48. As in the first embodiment, the diameter of the opening 40 on front side 42 is larger than the diameter of the opening 40 on back side 44, and the tongue 46 extends inwardly from outer edge 41 toward the back side 44. On the cone-shaped margin of opening 40 between edges 41 and 43 is formed a notch 48. Tongue 46 extends resiliently across opening 40 to cause suture thread 12 to engage notch 48 when tongue 46 is deflected by suture thread 12. When suture thread 12 is passed through opening 40, suture thread 12 deflects tongue 46 away from notch 48 toward back side 44. Thus suture thread 12 deviates around or below tongue 46. When the suture thread 12 is pulled with the needle 14 through opening 40 from front side 42 to back side 44, suture thread 12 may pass freely. When suture thread 12 is pulled in any other direction, most notably in a direction from back side 44 toward front side 42, tongue 46 is pulled or biased toward notch 48, locking suture thread 12 in my improved self locking suture lock 10'. Next, the suture needle 14 and suture thread 12 are brought through the tissue to be sutured in the conventional manner. Third, the suture needle 14 and suture thread 12 are threaded through the second stitch lock opening 50 which is similar to opening 40. Second opening 50 has a tongue 56, an outer edge 51, an inner edge 53, and a notch 58. The diameter of opening 50 on back side 44 is larger than the diameter of opening 50 on front side 42 and the tongue 56 extends inwardly from outer edge 51 toward the front side 42. On the cone-shaped margin of opening 50 between edges 51 and 53 is formed the notch 58. Tongue 56 extends resiliently across opening 50 to cause thread 12 to engage notch 58 when tongue 56 is deflected by suture thread 12. When suture thread 12 is passed through opening 50, suture thread 12 deflects tongue 56 away from notch 48 toward front side 42. Thus suture thread 12 deviates around tongue 56. When suture thread 12 is pulled with needle 14 through opening 50 from back side 44 to front side 42, suture thread 12 may pass freely. When suture thread 12 is pulled in any other direction, most notably in a direction from front side 42 toward back side 44, tongue 56 is pulled or biased toward notch 58 locking suture thread 12 in my improved self locking suture lock 10', again without the need for a surgical knot or for a second surgeon to assist in tieing one or more knots if the operation is performed laparoscopically. Again, front side 42 of opening 40 and back side 44 of opening 50 are desirably colored differently than the remainder of the improved self locking suture lock 10' to facilitate distinguishing between front side 42 and back side 44.

Referring to FIG. 5, the gathering and locking condition of suture thread 12 is shown when suture thread 12 is pulled against a tongue within a suture thread lock opening.

Referring to FIG. 6, another alternative embodiment of my improved self locking suture lock 10" is shown. The embodiment 10" is identical to the first embodiment 10 except that the suture material 12 is connected to the improved self locking suture lock 10". While FIG. 6 shows an end 13 of the suture material 12 connected to the base 16 of the self locking suture lock 10", it is to be understood that any portion of the suture material 12 could be connected to any portion of the self locking suture lock 10".

The surgeon first passes the self locking suture lock 10" having suture material 12 attached thereto through the laparoscopic tube to the surgical site. To begin suturing, the surgeon passes the suture material 12, having a needle 14 attached at the opposite end, through the tissue to be sutured. When the surgeon reaches the point of closing off a line of tissue or a cuff, the needle 14 and suture material 12 are passed through the lower suture lock opening 20. When a second line of tissue has been sutured and suturing is complete, the surgeon finishes the process by passing the needle 14 and suture material 12 through the upper suture lock opening 30. If additional sutures are required and a sufficient amount of suture material 12 remains unused, the surgeon may introduce the embodiment of my invention shown in FIG. 4 to the surgical site. Alternatively, the surgeon may pass another embodiment as shown in FIG. 6 through the laparoscopic tube in order to place more sutures at the surgical site.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method for using a one-piece self locking suture lock with suture material at a surgical site by utilizing a laparoscopic tube, the self locking suture lock including a body having a front side, a back side, a first stitch lock opening, and a second stitch lock opening; said first stitch lock opening being cone-shaped, having an outer edge, and having a larger diameter on said front side and a smaller diameter on said back side; said second stitch lock opening being cone-shaped, having an outer edge, and having a larger diameter on said back side and a smaller diameter on said front side; said first stitch lock opening having an integral tongue connected to said outer edge of said first stitch lock opening near said front side and extending diametrically at an angle from said front side toward said back side; said second stitch lock opening having an integral tongue connected to said outer edge of said second stitch lock opening near said back side and extending diametrically at an angle from said back side toward said front side, said method comprising the steps of:

passing said self locking suture lock through said laparoscopic tube to said surgical site;

threading said suture material through said first opening in said self locking suture lock;

passing said suture material through the tissue to be sutured;

threading said suture material through said second opening in said self locking suture lock.

2. The method of claim 1 further including the step of passing an additional self locking suture lock through said laparoscopic tube to said surgical site for an additional suture.

* * * * *